(12) United States Patent
Kamada

(10) Patent No.: US 10,391,286 B2
(45) Date of Patent: Aug. 27, 2019

(54) BILIARY TRACT DRAINAGE TUBE

(71) Applicant: NATIONAL UNIVERSITY CORPORATION KAGAWA UNIVERSITY, Takamatsu-shi, Kagawa (JP)

(72) Inventor: Hideki Kamada, Kagawa (JP)

(73) Assignee: NATIONAL UNIVERSITY CORPORATION KAGAWA UNIVERSITY, Takamatsu-shi, Kagawa (JP)

(*) Notice: Subject to any disclaimer, the term of this patent is extended or adjusted under 35 U.S.C. 154(b) by 287 days.

(21) Appl. No.: 15/123,443

(22) PCT Filed: Feb. 24, 2015

(86) PCT No.: PCT/JP2015/055194
§ 371 (c)(1),
(2) Date: Sep. 2, 2016

(87) PCT Pub. No.: WO2015/133333
PCT Pub. Date: Sep. 11, 2015

(65) Prior Publication Data
US 2017/0080193 A1    Mar. 23, 2017

(30) Foreign Application Priority Data
Mar. 3, 2014 (JP) .................. 2014-040139

(51) Int. Cl.
*A61M 27/00* (2006.01)
*A61B 1/018* (2006.01)

(52) U.S. Cl.
CPC .......... *A61M 27/002* (2013.01); *A61B 1/018* (2013.01); *A61M 2027/004* (2013.01); *A61M 2210/1075* (2013.01)

(58) Field of Classification Search
CPC .......... A61M 27/002; A61M 2027/004; A61M 2027/1075; A61B 1/028; A61B 2017/12059; A61B 2017/12068–12077
See application file for complete search history.

(56) References Cited

U.S. PATENT DOCUMENTS

2005/0085891 A1   4/2005  Goto et al.
2005/0085892 A1*  4/2005  Goto .................. A61F 2/94
                                             623/1.12

(Continued)

FOREIGN PATENT DOCUMENTS

JP    2009-136676 A    6/2009
JP    2013-505081 A    2/2013

(Continued)

OTHER PUBLICATIONS

International Search Report of PCT/JP2015/055194.

*Primary Examiner* — Benjamin J Klein
(74) *Attorney, Agent, or Firm* — Muncy, Geissler, Olds & Lowe, P.C.

(57) ABSTRACT

[Subjects] To provide a biliary tract drainage tube in which both an external drainage tube and an internal drainage tube can be installed in a single endoscopic procedure.
[Method to Solve]
A biliary tract drainage tube used to drain a biliary tract is provided with long external drainage tube 2 and internal drainage tube 3 that is provided on the tip of the external drainage tube so as to be separable from the external drainage tube. Both external drainage tube 2 and internal drainage tube 3 are placed in biliary tract Cd. Since internal drainage tube 3 can be left behind in the biliary tract by removing external drainage tube 2, another endoscopic procedure is not required when switching from external (Continued)

drainage tube 2 to internal drainage tube 3, and the burden placed on the patient can be lessened.

18 Claims, 6 Drawing Sheets

(56) References Cited

U.S. PATENT DOCUMENTS

2006/0276873 A1* 12/2006 Sato .................. A61B 17/3468
  623/1.11
2015/0005804 A1* 1/2015 Franano ........... A61B 17/12113
  606/195

FOREIGN PATENT DOCUMENTS

| JP | 2006-149576 A | 6/2016 |
| WO | 2003/092782 A1 | 11/2003 |

* cited by examiner

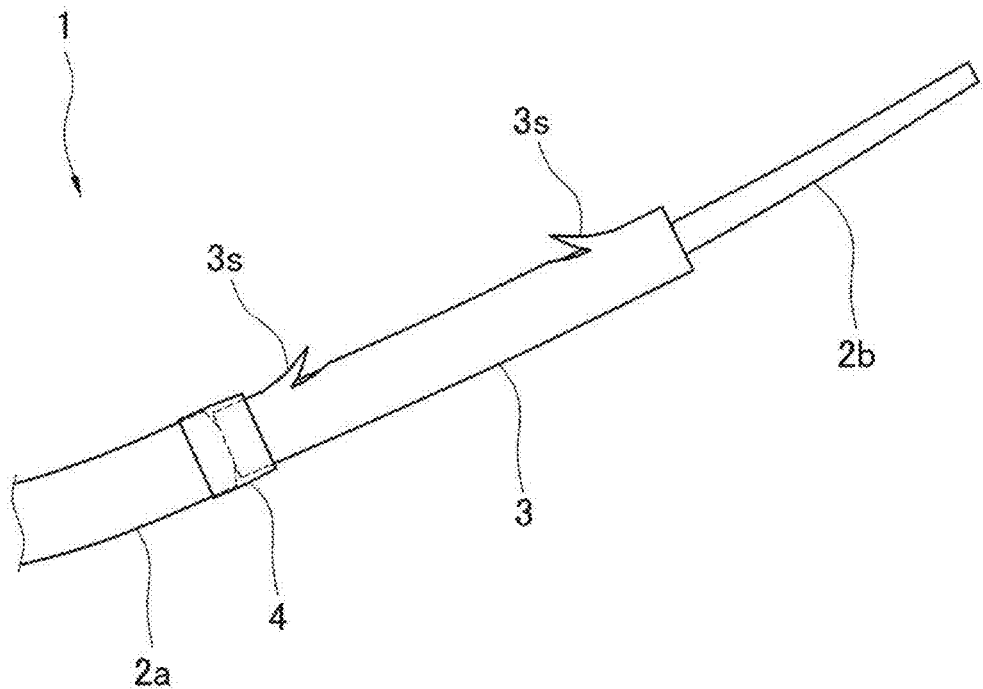
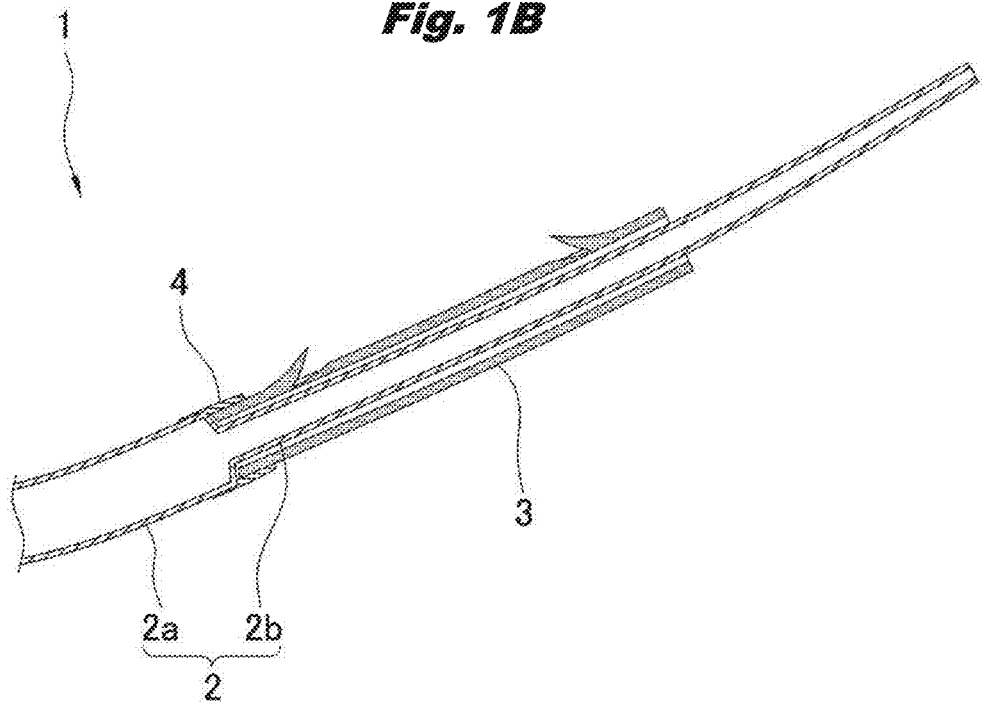

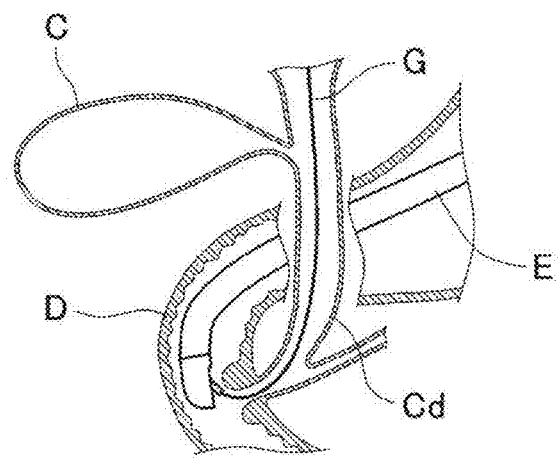
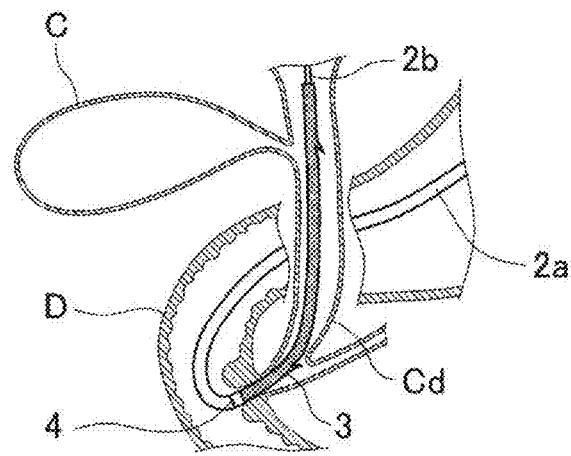
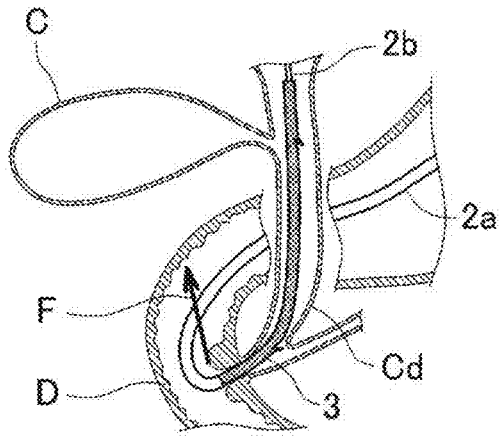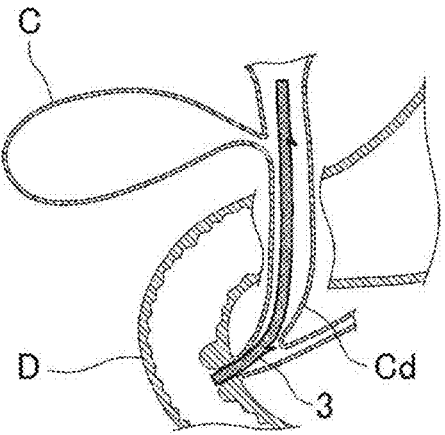

External Drainage Tube

Internal Drainage Stent

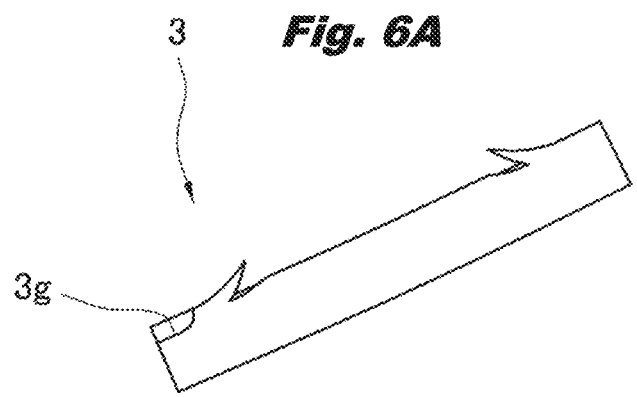
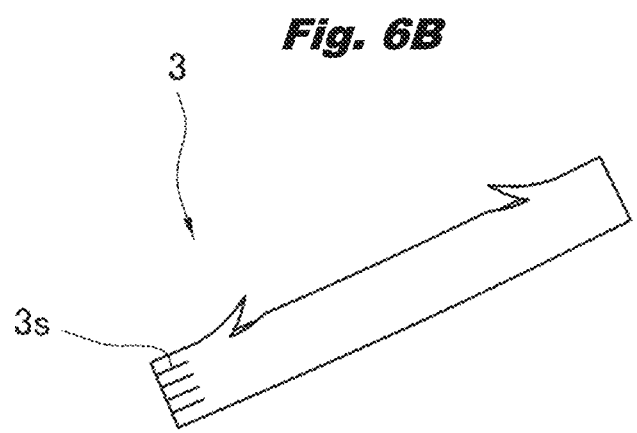
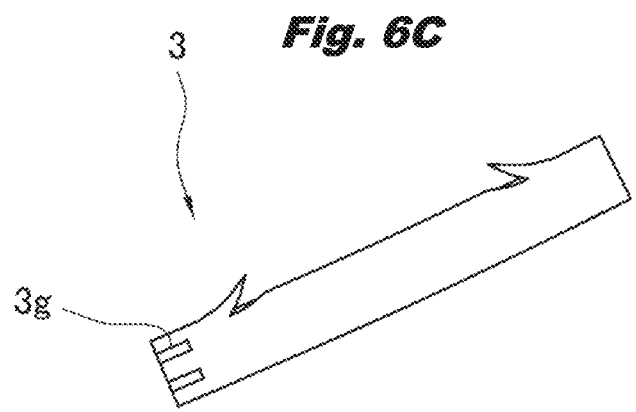

BILIARY TRACT DRAINAGE TUBE

CROSS REFERENCE TO RELATED APPLICATIONS

This application is a national stage of International Application No.: PCT/JP2015/055194, which was filed on Feb. 24, 2015, and which claims priority to JP 2014-040139 which was filed on Mar. 3, 2014, and which are both herein incorporated by reference.

TECHNICAL FIELD

The present invention relates to a biliary tract drainage tube. More specifically, the present invention relates to a biliary tract drainage tube used as a conduit for draining bile extracorporeally or into the duodenum.

BACKGROUND ART

Bile is a liquid produced by the liver that flows into the duodenum via the bile duct, hepatic ducts, gallbladder, and common bile duct. In the duodenum, bile activates digestive enzymes in pancreatic fluid and together with the pancreatic fluid breaks down fats and proteins so that they can be readily absorbed by the intestines. Because fatty acids that cannot be broken down by fats are not readily absorbed, bile acts to convert these fatty acids into an easy-to-absorb form.

The flow of bile slows down when a biliary obstruction occurs, but the liver continues to produce bile even when the flow of bile slows down. When the amount of bile produced by the liver exceeds the amount of bile flowing into the duodenum, bile is stored in the gallbladder. However, when the gallbladder becomes full, some of the bile produced by the liver accumulates in the liver. When bile flows into the duodenum, it performs the function described above. However, when bile accumulates in the liver, tissue is destroyed. This can even cause cirrhosis of the liver. Therefore, when a biliary obstruction happens, pressure relief (drainage) has to occur in the biliary tract to improve the flow of bile.

One method of draining the biliary tract is to place a tube in the biliary tract using an endoscope to form a flow path for the bile. In this method, there is an external drainage technique in which one end of a long drainage tube (external drainage tube) is placed in the biliary tract and the other end is drawn from the body via the nose to discharge bile extracorporally [see FIG. 4 (A)], and an internal drainage technique in which a short tube (internal drainage tube) is placed in the body to connect the bile duct to the duodenum and allow bile to flow intracorporeally (that is, into the duodenum) [see FIG. 4 (B)].

The external drainage technique is advantageous from the standpoint of observing the drainage effect because bile discharge conditions and discharge amounts can be grasped. However, in the external drainage technique, the external drainage tube passes through the nose, and the container used to collect the discharged bile has to be carried around all the time. This makes the patient uncomfortable. Therefore, a switch is made from the external drainage tube to an internal drainage tube once it has been determined that the purposes of the drainage have been adequately achieved.

When the switch is made from the external drainage tube to an internal drainage tube, a procedure is performed in which the external drainage tube is removed, an endoscope is inserted, and an internal drainage tube is installed. Insertion of an endoscope is somewhat painful to the patient, so it has to be performed as quickly as possible.

Various devices have been disclosed for placement of an internal drainage tube (see, for example, Patent Document 1 and Patent Document 2), and a medical device for performing this procedure quickly has been realized in the 'Rapid Exchange Biliary Stent System' from Boston Scientific Japan.

PRIOR ART TECHNICAL DOCUMENTS

Patent Documents

[Patent Doc. 1] Japanese Patent Publication 2013-505081, which is a translation of PCT International Application

[Patent Doc. 2] Japanese Laid-Open Patent Publication 2009-136676

SUMMARY OF THE INVENTION

Subject Solved by the Invention

However, placement of an external drainage tube and an internal drainage tube requires an endoscopic procedure. As mentioned above, most endoscopic procedures are painful, and the burden placed on patients means the number of procedures must be minimized.

However, conventional internal drainage tubes, including those in the techniques disclosed in Patent Document 1, Patent Document 2, and the 'Rapid Exchange Biliary Stent System', are placed in the biliary tract after the external drainage tube has been removed. This means a minimum of two endoscopic procedures must be performed to install an internal drainage tube. Installation of both the external drainage tube and the internal drainage tube in a single endoscopic procedure would be preferable, but a medical device able to perform such a procedure has not been developed.

In view of this situation, it is an object of the present invention to provide a biliary tract drainage tube in which both an external drainage tube and an internal drainage tube can be installed in a single endoscopic procedure.

Method to Solve the Subject

A biliary tract drainage tube of the first invention used to drain a biliary tract comprises: a long external drainage tube that is inserted from one of a nose and mouth to be placed in a digestive tract, and an internal drainage tube that is provided on a tip of the external drainage tube so as to be separable from the external drainage tube.

A biliary tract drainage tube of the second invention is characterized that, based on the first invention, the internal drainage tube is attached to the external drainage tube in a state where the internal drainage tube is inserted into the tip of the external drainage tube.

A biliary tract drainage tube of the third invention is characterized that, based on the second invention, the external drainage tube comprises a main body portion and a narrow-diameter portion that is provided in a tip portion of the main body portion, the narrow-diameter portion is formed so as to have an outer diameter that is narrower than an outer diameter of the main body portion and an inner diameter of the internal drainage tube, and the internal drainage tube is attached to the external drainage tube in a state where the narrow-diameter portion of the external drainage tube is inserted into the inner diameter tube.

A biliary tract drainage tube of the fourth invention is characterized in, based on the first, second and third inventions, further comprising a detachment-preventing portion for preventing detachment of the internal drainage tube.

A biliary tract drainage tube of the fifth invention is characterized that, based on the fourth invention, the detachment-preventing portion connects the internal drainage tube and the external drainage tube, and is made of a material that dissolves in a patient body.

A biliary tract drainage tube of the sixth invention is characterized that, based on the fifth invention, the detachment-preventing portion is threads, tape, and/or an adhesive connecting the internal drainage tube and the external drainage tube.

A biliary tract drainage tube of the seventh invention is characterized that, based on the third invention, the narrow-diameter portion of the external drainage tube has a length in an axial direction that is greater than a length of the internal drainage tube, and includes a detachment-preventing portion for preventing detachment of the internal drainage tube, the detachment-preventing portion is a portion that is provided in the narrow-diameter portion of the external drainage tube whose diameter is greater than the inner diameter of the internal drainage tube, is provided at a position protruding from a tip of the internal drainage tube in a state where the internal drainage tube is attached, and has a structure of which a diameter is reducible by an external stimulus.

A biliary tract drainage tube of the eighth invention is characterized that, based on the seventh invention, the detachment-preventing portion is formed by deforming the narrow-diameter portion of the external drainage tube and is made of a material having less rigidity than a guide wire.

A biliary tract drainage tube of the ninth invention is characterized that, based on the seventh or eighth invention, the detachment-preventing portion is the narrow-diameter portion of the external drainage tube that is formed in a spiral shape.

A biliary tract drainage tube of the tenth invention is characterized that, based on the first invention, a connecting portion is provided for connecting the internal drainage tube and the external drainage tube, the connecting portion is configured so that the connection between the internal drainage tube and the external drainage tube can be severed by ultrasonic stimulation.

A biliary tract drainage tube of eleventh invention is characterized that, based on the tenth invention, the internal drainage tube and the external drainage tube are formed from a single continuous tube.

A biliary tract drainage tube of the twelfth invention is characterized in comprising a main body portion that is inserted from one of a nose and mouth to be placed in a digestive tract, and a narrow-diameter portion that is provided on a tip of the main body portion, wherein the narrow-diameter portion has an outer diameter that is narrower than an outer diameter of the main body portion and an inner diameter of an internal drainage tube.

A biliary tract drainage tube of the thirteenth invention is characterized that, based on the twelfth invention, a detachment-preventing portion is formed in the narrow-diameter portion to prevent detachment of the internal drainage tube.

A biliary tract drainage tube of the fourteenth invention is characterized that, based on the thirteenth invention, the narrow-diameter portion has a length in an axial direction that is greater than a length of the internal drainage tube, and the detachment-preventing portion is a portion whose diameter is greater than an inner diameter of the internal drainage tube, and is provided at a position protruding from a tip of the internal drainage tube in a state where the internal drainage tube is attached, and has a structure of which a diameter is reducible by an external stimulus.

A biliary tract drainage tube of the fifteenth invention is characterized that, based on the fourteenth invention, the detachment-preventing portion is formed by deforming the narrow-diameter portion of the external drainage tube and is made of a material having less rigidity than a guide wire.

A biliary tract drainage tube of the sixteenth invention is characterized that, based on the fourteenth invention, the detachment-preventing portion is the narrow-diameter portion of the external drainage tube that is formed in a spiral shape.

A biliary tract drainage tube of the seventeenth invention is characterized that, based on any of the first through eleventh inventions, the internal drainage tube has a slit and/or notch formed in one end thereof, the slit and/or notch extending in an axial direction from the one end.

Effect of the Invention

In the first through third aspects of the present invention, when a tip of the external drainage tube is placed in a bile duct by an endoscope that were inserted into a digestive tract from a patient mouth, the external drainage tube is placed in the digestive tract in a state where the external drainage tube is inserted from one of the patient's nose and mouth, and both the external drainage tube and the internal drainage tube can be placed in the bile duct with the internal drainage tube provided on the tip of the external drainage tube. Here, the internal drainage tube can be left behind in the bile duct by removing the external drainage tube after both the external drainage tube and the internal drainage tube have been placed in the bile duct. Therefore, another endoscopic procedure is not required to switch from the external drainage tube to the internal drainage tube, and the burden placed on the patient can be lessened.

In the fourth aspect of the present invention, a detachment-preventing portion is provided to prevent detachment of the internal drainage tube. This makes endoscopic placement of the tip of the external drainage tube in the bile duct with the internal drainage tube attached to the external drainage tube easier.

In the fifth aspect of the present invention, the detachment-preventing portion is made of a material that dissolves in the body. As a result, the internal drainage tube and the external drainage tube become disconnected once a certain amount of time has passed after placement of the tubes. Therefore, no special operation is required to disconnect the internal drainage tube from the external drainage tube and remove the external drainage tube, lessening the burden on both the surgeon and the patient.

In the sixth aspect of the present invention, the internal drainage tube and the external drainage tube can be connected to each other securely by the detachment-preventing portion.

In the seventh embodiment of the present invention, the internal drainage tube can be kept from becoming detached from the narrow-diameter portion of the external drainage tube by the detachment-preventing portion. Because the diameter of the detachment-preventing portion can be reduced by the application of an external stimulus, the external drainage tube can be removed while leaving behind the internal drainage tube.

In the eighth aspect of the present invention, a guide wire is passed through the external drainage tube to the detachment-preventing portion and the shape of the guide wire is used to deform the detachment-preventing portion. Because the detachment-preventing portion is straightened and can pass through the internal drainage tube, the external drainage tube can be removed while leaving behind the internal drainage tube.

In the ninth aspect of the present invention, the detachment-preventing portion is the narrow-diameter portion formed in a spiral shape. As a result, the detachment-preventing portion can act as a stopper securing the external drainage tube inside the bile duct.

In the tenth aspect of the present invention, the internal drainage tube and the external drainage tube can be connected by a connecting portion. This can keep the internal drainage tube from becoming detached from the external drainage tube. Because the connecting portion of the internal drainage tube and the external drainage tube are separated by the external application of ultrasonic stimulation, the external drainage tube can be removed while leaving behind the internal drainage tube.

In the eleventh aspect of the present invention, the internal drainage tube and the external drainage tube are formed from a single continuous tube. As a result, the internal drainage tube does not detach from the external drainage tube.

In the twelfth aspect of the present invention, when a tip of the external drainage tube is placed in a biliary tract by an endoscope that were inserted into a digestive tract from a patient mouth, the external drainage tube is placed in the digestive tract in a state where the external drainage tube is inserted from one of the patient's nose and mouth, both the external drainage tube and the internal drainage tube can be placed in the bile duct with the internal drainage tube attached to the external drainage tube. When the external drainage tube is removed after both the external drainage tube and the internal drainage tube have been placed in the bile duct, the internal drainage tube can be left behind in the bile duct. Therefore, the switch can made from the external drainage tube to the internal drainage tube without requiring another endoscopic procedure. This can lessen the burden on the patient.

In the thirteenth aspect of the present invention, a detachment-preventing portion is provided to prevent detachment of the internal drainage tube. As a result, the tip of the external drainage tube can be easily installed in the bile duct using an endoscope with the internal drainage tube attached to the narrow-diameter portion of the external drainage tube.

In the fourteenth aspect of the present invention, detachment of the internal drainage tube from the narrow-diameter portion of the external drainage tube can be prevented using a detachment-preventing portion. Because the diameter of the detachment-preventing portion can be reduced by the application of an external stimulus, the external drainage tube can be removed while leaving behind the internal drainage tube.

In the fifteenth aspect of the present invention, a guide wire is passed through the external drainage tube to the detachment-preventing portion and the shape of the guide wire is used to deform the detachment-preventing portion. Because the detachment-preventing portion is straightened and can pass through the internal drainage tube, the external drainage tube can be removed while leaving behind the internal drainage tube.

In the sixteenth aspect of the present invention, the detachment-preventing portion is the narrow-diameter portion formed in a spiral shape. As a result, the detachment-preventing portion can act as a stopper securing the external drainage tube inside the bile duct.

In the seventeenth aspect of the present invention, the force applied to the base end of the internal drainage tube to remove the external drainage tube can be reduced even when the force is applied to the base end of the internal drainage tube in the radial direction. This can help keep the internal drainage tube from coming out when the external drainage tube is removed.

BRIEF DESCRIPTION OF THE DRAWINGS

FIG. 1 is a pair of enlarged drawings used to explain the tip portions of the biliary tract drainage tube 1 in an embodiment of the present invention, in which FIG. 1 (A) is a side view, and FIG. 1 (B) is a cross-sectional view of the internal drainage tube 3.

FIG. 2 is a set of side views used to explain the drainage of the biliary tract using the biliary tract drainage tube 1 in the embodiment of the present invention.

FIG. 6 is a drawing used to explain the internal drainage tube 3 in another embodiment of the present invention.

EMBODIMENT OF THE INVENTION

The following is an explanation of embodiments of the present invention with reference to the drawings. The biliary tract drainage tube of the present invention is a tube placed in the bile duct when, for example, obstructive jaundice occurs due, for example, to a stone or tumor in the bile duct. The present invention is characterized by the ability to install an internal drainage tube at the same time as an external drainage tube.

(Explanation of Biliary Tract Drainage)

First, placement of a biliary tract drainage tube 1 in an embodiment of the present invention for the external drainage technique will be briefly explained before explaining the biliary tract drainage tube 1 itself.

When biliary tract drainage is performed using the external drainage technique, an endoscope E is inserted via a mouth and the tip of the endoscope E is positioned in the duodenum D, that is, positioned near the outlet of the common bile duct Cd. Next, a guide wire G made of a rigid material such as a metal is passed via the forceps hole in the endoscope E as far as the duodenum D. Then, the tip portion of the guide wire G is inserted into the bile duct [see FIG. 2 (A)]. When the tip portion of the guide wire G has reached a predetermined position in the common bile duct Cd, a biliary tract drainage tube 1 is placed over the guide wire G and the tip portion of the biliary tract drainage tube 1 is guided to its intended portion. Then, the endoscope E is removed and the biliary tract drainage tube 1 is left in place. Finally, a guide tube is inserted via the nose, and the biliary tract drainage tube 1 emerging from the mouth is guided into the nose to complete the installation of the biliary tract drainage tube 1 [see FIG. 2 (B)]. Afterwards, bile can be discharged extracorporeally via the biliary tract drainage tube 1.

(Biliary Tract Drainage Tube 1 in the Present Embodiment)

The following is an explanation of the biliary tract drainage tube 1 in the present embodiment.

As shown in FIG. 1, the biliary tract drainage tube 1 in the present embodiment comprises an external drainage tube 2, an internal drainage tube 3 attached to the tip of the external drainage tube 2, and a detachment-preventing portion 4 connecting the external drainage tube 2 to the internal drainage tube 3.

(External Drainage Tube 2)

Figure 4A:
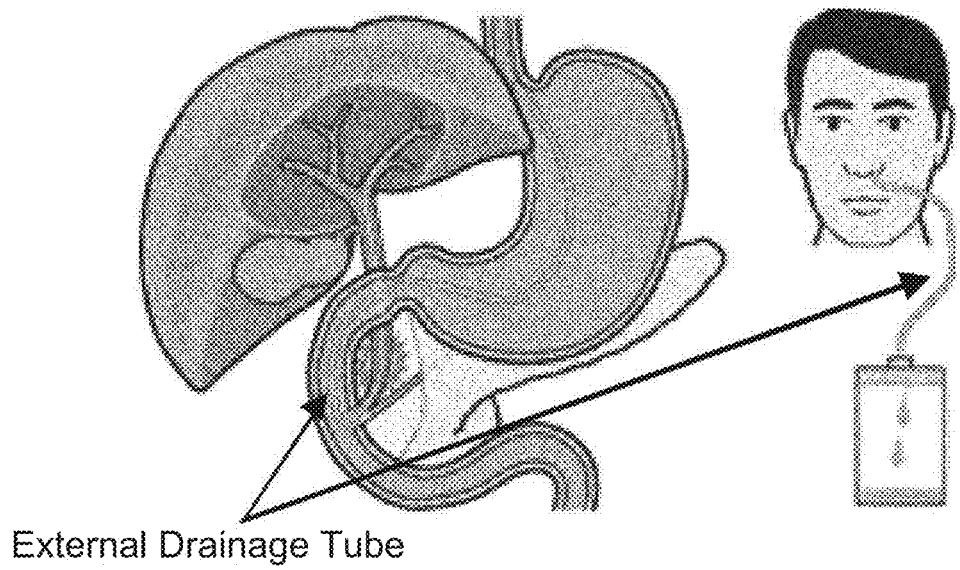
FIG. 4 is a pair of drawings used to explain biliary tract drainage, in which FIG. 4 (A) is used to explain the external drainage technique, and FIG. 4 (B) is used to explain the internal drainage technique.
Figure 4B:
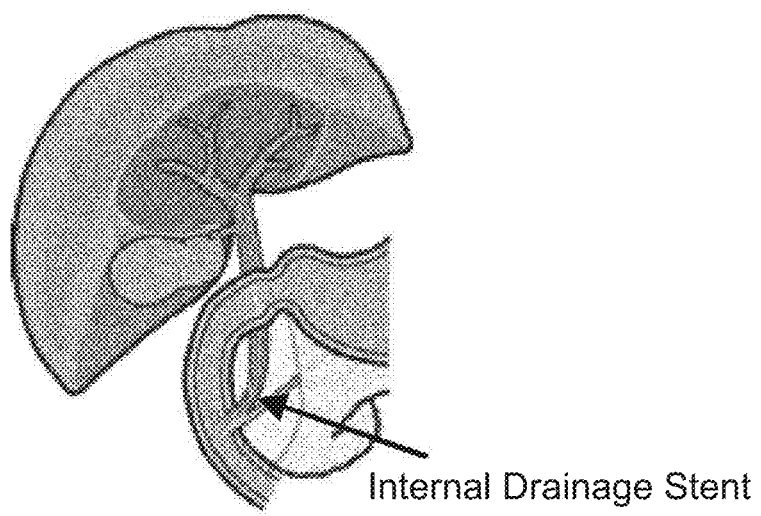

The external drainage tube 2 is a long tube comprising a main body portion 2a and a narrow-diameter portion 2b provided on the tip of the main body portion 2a. The main body portion 2a has a structure similar to a conventional external drainage tube. More specifically, the main body portion 2a has a length of from 2,300 to 2,350 mm, an outer diameter of from 2.7 to 3.3 mm (8 to 10 Fr), and an inner diameter of from 2.0 to 2.8 mm (6 to 8.5 Fr). In other words, the main body portion 2a is formed so as to have an outer diameter allowing the tube to be passed through the forceps hole in an endoscope E and into the common bile duct Cd, and so as to have a length allowing the base end of the tube to pass out of the body via the nose while the tip remains in place inside the common bile duct Cd [see FIG. 4 (A)].

The narrow-diameter portion 2b of the external drainage tube 2 is a tubular portion whose outer diameter is narrower than the outer diameter of the main body portion 2a. More specifically, the narrow-diameter portion 2b has an outer diameter of from 1.7 to 2.0 mm (5 to 6 Fr) and an inner diameter of from 1.2 to 1.5 mm (3.6 to 4.5 Fr). In other words, the narrow-diameter portion 2b is formed so as to have an outer diameter that is narrower than the outer diameter of the main body portion 2a and so as to have an inner diameter large enough to pass over the guide wire G. The inner diameter of the narrow-diameter portion 2b is preferably able to perform this function while also being large enough to allow for the smooth flow of bile. For example, the narrow-diameter portion 2b can be smoothly inserted over the guide wire G while also enabling bile to be smoothly introduced when the inner diameter of the narrow-diameter portion 2b is from 1.2 to 1.5 mm (3.6 to 4.5 Fr).

In the external drainage tube 2, there are no particular restrictions on the shape of the connecting portion between the main body portion 2a and the narrow-diameter portion 2b. For example, when it has tiers as shown in FIG. 1, the tiered portion can come into contact with and hold the internal drainage tube 3 in place to enable stable installation of the internal drainage tube 3.

The connecting portion may also be tapered. Here, when the internal drainage tube 3 is pushed into the tapered portion, the internal drainage tube 3 can be connected to the main body portion 2a of the external drainage tube 2 by applying a certain amount of connecting force.

(Internal Drainage Tube 3)

The internal drainage tube 3 is a short tube having a length comparable to that of an internal drainage tube (internal drainage stent) used in the conventional internal drainage technique. More specifically, the internal drainage tube 3 is formed so that the base end protrudes into the duodenum D with the tip of the internal drainage tube 3 arranged near the intrahepatic bile ducts when the internal drainage tube 3 has been placed inside the common bile duct Cd. There are no particular restrictions on the length of the internal drainage tube 3, but a length of from 70 to 150 mm is preferred, and a length of from 90 to 120 mm is especially preferred.

Also, the internal drainage tube 3 is formed so as to have an outer diameter of from 2.0 to 2.7 mm (6 to 8 Fr) and an inner diameter of from 1.8 to 2.5 mm (5.4 to 7.5 Fr). In other words, the internal drainage tube 3 is formed so as to have an inner diameter greater than the narrow-diameter portion 2b of the external drainage tube 2 and an outer diameter equal to or smaller than the outer diameter of the main body portion 2a of the external drainage tube 2. As a result, the internal drainage tube 3 can be attached to the narrow-diameter portion 2b of the external drainage tube 2, and the external drainage tube 2 can be placed in the common bile duct Cd without any hindrance even when an internal drainage tube 3 is provided.

A flange 3s is provided on the internal drainage tube 3 to secure the internal drainage tube 3 inside the common bile duct Cd so as not to move.

(Detachment-Preventing Portion 4)

As shown in FIG. 1, a detachment-preventing portion 4 is provided between the base end of the internal drainage tube 3 and the tip portion of the main body portion 2a of the external drainage tube 2. The detachment-preventing portion 4 is connected to both the internal drainage tube 3 and the main body portion 2a of the external drainage tube 2. In FIG. 1, the detachment-preventing portion 4 is formed by a sheet-like member, and the base end of the internal drainage tube 3 and the tip portion of the main body portion 2a of the external drainage tube 2 are secured by winding the detachment-preventing portion 4 around both of them.

Here, the detachment-preventing portion 4 is made of a material that dissolves in the body. For example, it may be made of a fat, protein, or water-soluble material that dissolves over several days in the presence of the digestive juices (bile and pancreatic fluid) inside the duodenum.

(Operations and Effects of the Biliary Tract Drainage Tube 1 in the Present Embodiment)

In a biliary tract drainage tube 1 of the present embodiment with the configuration described above, both the external drainage tube 2 and the internal drainage tube 3 can be placed inside the bile duct. In other words, both the external drainage tube 2 and the internal drainage tube 3 can be placed inside the bile duct by placing the tip of the external drainage tube 3 in the bile duct using an endoscope E with the internal drainage tube 3 attached to the narrow-diameter portion 2b of the external drainage tube 2.

In addition, a detachment-preventing portion 4 is provided to prevent detachment of the internal drainage tube 3 from the narrow-diameter portion 2b of the external drainage tube 2. By attaching the internal drainage tube 3 to the narrow-diameter portion 2b of the external drainage tube 2, the risk of the internal drainage tune 3 becoming detached when the external drainage tube 2 is placed in the bile duct can be reduced. As a result, the tip of the external drainage tube 2 with the internal drainage tube 3 attached can be easily placed in the bile duct using an endoscope E.

Because the detachment-preventing portion 4 is made of a material that dissolves in the body, the detachment-preventing portion 4 dissolves and the external drainage tube 2 becomes detached from the internal drainage tube 3 once a certain amount of time has passed after the biliary tract drainage tube 1 of the present embodiment was placed in the body. At this time, the internal drainage tube 3 and the external drainage tube 2 can move freely with respect to each other [see FIG. 2 (C)]. When biliary tract drainage using the external drainage tube 2 has ended and the external drainage tube 2 is removed, the external drainage tube 2 can be removed while leaving the internal drainage tube 3 behind in the common bile duct Cd [see FIG. 2 (D)]. In other words, when the biliary duct drainage tube 1 of the present embodiment is switched from the external drainage technique to the internal drainage technique, an endoscopic procedure is not required. This lessens the burden on the patient.

(Detachment-Preventing Portion 4)

The detachment-preventing portion 4 used to connect the internal drainage tube 3 to the external drainage tube 2 does not have to be the sheet-like member described above. For example, the internal drainage tube 3 and the external drainage tube 2 can be sutured together using medical thread (absorbed thread) not requiring stitching. The internal drainage tube 3 and the external drainage tube 2 may also be bonded together using an adhesive that dissolves in the body. In these cases, the medical thread or adhesive dissolves and the external drainage tube 2 and the internal drainage tube 3 become detached once a certain amount of time has passed after the biliary tract drainage tube 1 of the present embodiment was placed in the body.

There are also no particular restrictions on the structure of the detachment-preventing portion as long as movement of the internal drainage tube 3 can be restricted. For example, thread fixed at one end to the internal drainage tube 3 and extending at the other end to the base end of the main body portion 2a of the external drainage tube 2 can serve as the detachment-preventing portion. In this case, when the thread is pulled so that the force causes the thread to pull away from the internal drainage tube 3 and break, the external drainage tube 2 can be disconnected from the internal drainage tube 3.

There are also no particular restrictions on how the detachment-preventing portion 4 connects the internal drainage tube 3 to the external drainage tube 2 as long as the internal drainage tube 3 can be kept from detaching from the external drainage tube 2.

Figure 3A:
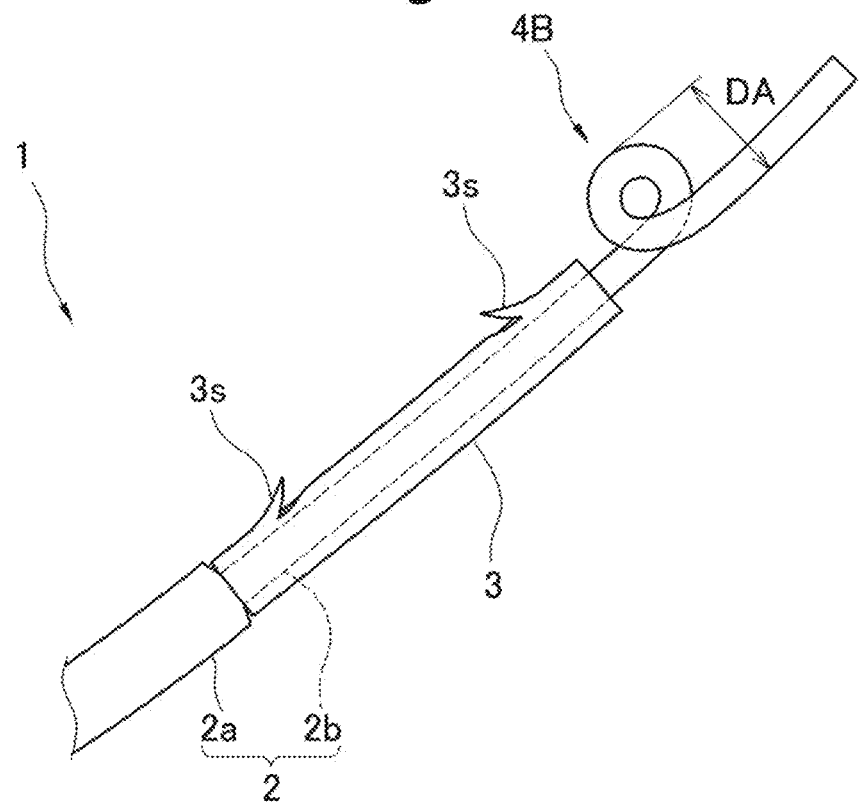
FIG. 3 is a pair of enlarged drawings used to explain the tip portions of the biliary tract drainage tube 1 in another embodiment of the present invention, in which FIG. 3 (A) is a side view showing the situation when a detachment-preventing portion 4B has been formed, and FIG. 3 (B) is a side view showing the situation when the detachment-preventing portion 4B has been stretched out.
Figure 3B:
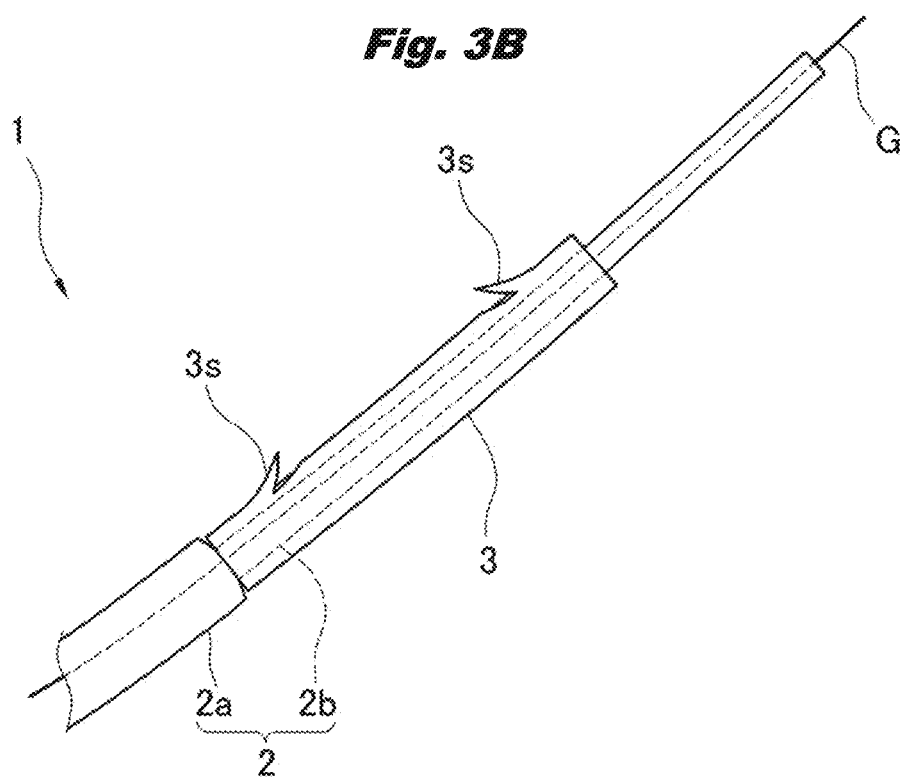

For example, the detachment-preventing portion 4 can be configured so that the narrow-diameter portion 2b of the external drainage tube 2 is deformed. More specifically, as shown in FIG. 3 (A), the detachment-preventing portion 4 may be a ring-shaped portion protruding from the tip of the internal drainage tube 3 when the internal drainage tube 3 is attached. In this case, the internal drainage tube 3 can be kept from becoming detached from the narrow-diameter portion 2b of the external drainage tube 2 if the outer diameter DA of the detachment-preventing portion 4B is greater than the inner diameter of the internal drainage tube 3.

In this configuration, the internal drainage tube 3 cannot become detached from the external drainage tube 2 unless the outer diameter DA of the detachment-preventing portion 4B becomes smaller than the inner diameter of the internal drainage tube 3. However, if the narrow-diameter portion 2b of the external drainage tube 2 is made of a material less rigid than the guide wire, the outer diameter DA of the detachment-preventing portion 4B can be made smaller than the inner diameter of the internal drainage tube 3 simply by passing a guide wire G to the external drainage tube 2. In other words, when the guide wire G is passed to the detachment-preventing portion 4B at the narrow-diameter portion 2b of the external drainage tube 2, the shape of the guide wire can be used to straighten out the detachment-preventing portion 4B [see FIG. 3 (B)]. Because the outer diameter of the narrow-diameter portion 2b is then smaller than the inner diameter of the internal drainage tube 3, the detachment-preventing portion 4B can pass into the external drainage tube. As a result, the external drainage tube 2 can be removed while leaving the internal drainage tube 3 behind even when a detachment-preventing portion 4B is provided on the narrow-diameter portion 2b of the external drainage tube 2.

Note that there are no particular restrictions on the shape of the detachment-preventing portion 4B formed in the narrow-diameter portion 2b of the external drainage tube 2 as long as the diameter is greater than the inner diameter of the internal drainage tube 3. For example, a detachment-preventing portion may be formed by forming a spiral in the narrow-diameter portion 2b. A detachment-preventing portion may also be formed simply by providing a spherical bulge (bulging diameter portion) in the narrow-diameter portion 2b. When a detachment-preventing portion is provided by forming a spiral in the narrow-diameter portion 2b, the detachment-preventing portion can act as a stopper securing the external drainage tube 2 inside the common bile duct Cd.

The method used to deform the detachment-preventing portion so that the narrow-diameter portion 2b of the external drainage tube 2 can pass through the internal drainage tube is not restricted to the use of a guide wire G as described above. For example, when the narrow-diameter portion 2b is made of a shape memory material which returns to its original shape at body temperature after placement in the body, the external drainage tube 2 can be placed in the common bile duct Cd even when the narrow-diameter portion 2b is bent or a bulging diameter portion is formed in the narrow-diameter portion 2b. This is because the narrow-diameter portion 2b becomes straight (or the large diameter portion disappears) after a certain amount of time has passed.

When a shape memory material is used which returns to its original shape at temperature higher (or lower) than room temperature, a liquid of a predetermined temperature can be supplied to the external drainage tube 2 to straighten out the narrow-diameter portion 2b or shrink the bulging diameter portion.

In other words, if the detachment-preventing portion has a structure in which the diameter (or length in the radial direction of the external drainage tube 2) can be reduced by an external stimulus, the detachment-preventing portion can prevent detachment of the internal drainage tube 3 from the narrow-diameter portion 2b of the external drainage tube 2, and the external drainage tube 2 can later be removed while leaving behind the internal drainage tube 3.

A detachment-preventing portion may also be provided that prevents detachment of the internal drainage tube 3 until the tip portion of the external drainage tube 2 has been placed inside the common bile duct Cd, that is, until the internal drainage tube 3 has been placed inside the common bile duct Cd. For example, if the connecting portion between the main body portion 2a and the narrow-diameter portion 2b of the external drainage tube 2 is tapered, the internal drainage tube 3 can be kept from detaching to a certain extent simply by pushing the internal drainage tube 3 into the tapered portion. Provision of detachment-preventing portion is desirable because a stable procedure can be performed if a detachment-preventing portion is provided.

(External Drainage Tube 2)

Figure 5A:
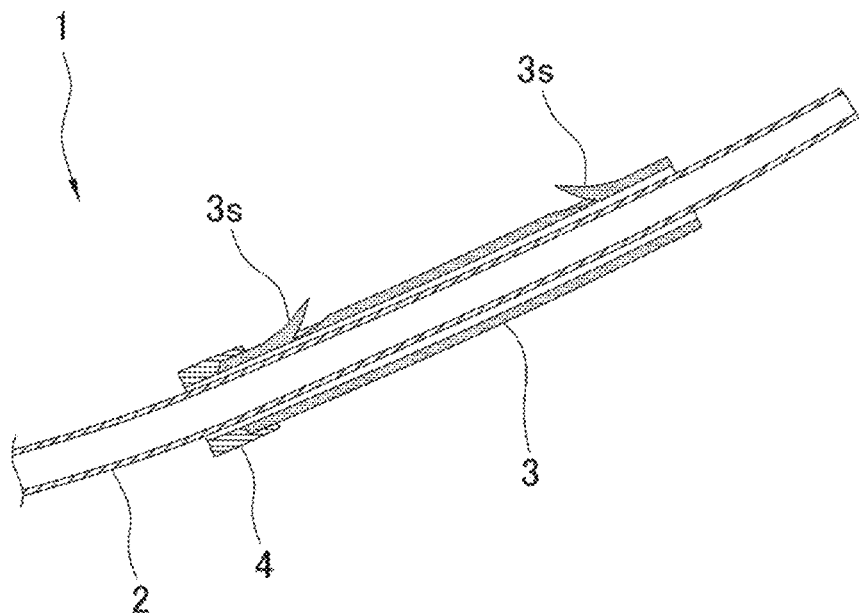
FIG. 5 is a pair of enlarged drawings used to explain the tip portions of the biliary tract drainage tube 1 in another embodiment of the present invention.
Figure 5B:
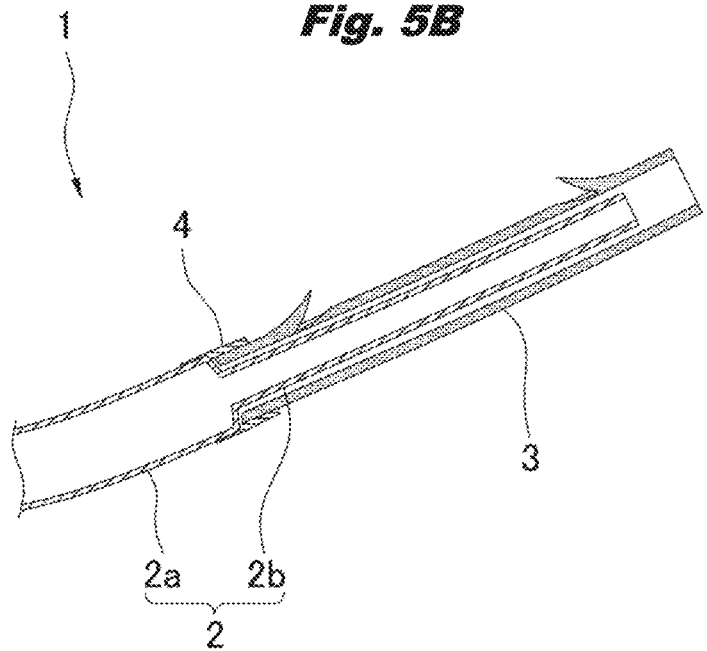

In the examples described above, the external drainage tube 2 had a main body portion 2a and a narrow-diameter portion 2b. When a narrow-diameter portion 2b is provided, the internal drainage tube 3 is more easily attached to the external drainage tube 2, and the internal drainage tube 3 is more easily installed in the common bile duct Cd. However, a narrow-diameter portion 2b does not have to be provided on the external drainage tube 2 if the tip can be installed in the common bile duct Cd with the internal drainage tube 3 attached to the tip. For example, a tube having an inner diameter (corresponding to the outer diameter of the main body portion 2a in the examples described above) larger than the outer diameter of the external drainage tube 2 can be used as the internal drainage tube 3B [see FIG. 5 (A)].

The biliary tract drainage tubes 1 explained in the examples are provided with an internal drainage tube 3 attached to the external drainage tube 2. However, the internal drainage tube 3 can be attached to the external drainage tube 2 just before the procedure. In this case, an internal drainage tube 3 can be selected with a shape and size adapted to the condition of the patient. In this case, the external drainage tube 2 can have a main body portion 2a and a narrow-diameter portion 2b or an external drainage tube 2 can be used which does not have a narrow-diameter portion 2b.

In the examples described above, the internal drainage tube 3 is inserted into the tip portion of the external drainage tube 2. However, the tip of the external drainage tube 2 can be connected to the base end of the internal drainage tube 3 using a connecting portion. For example, the tip of the external drainage tube 2 and the base end of the internal drainage tube 3 abutting each other can be secured to each other using a sheet-like member (connecting portion) [see FIG. 5 (B)].

Also, the external drainage tube 2 and the internal drainage tube 3 can be formed as a single unit and the interface portion between them can be formed so as to separate when subjected to ultrasonic stimulation. In this case, the connecting portion between the internal drainage tube 3 and the external drainage tube 2 is subjected to external ultrasonic stimulation and severed so that the external drainage tube 2 can be removed while leaving the internal drainage tube 3 in place. Because the internal drainage tube 3 and the external drainage tube 2 are formed from a single continuous tube, the internal drainage tube 3 does not become detached from the external drainage tube 2.

(Internal Drainage Tube)

A slit or notch may be formed in the base end of the internal drainage tube [see FIG. 6]. When the external drainage tube 2 is removed, force is applied to the base end of the internal drainage tube 3 in the radial direction [see FIG. 3 (C)]. The internal drainage tube 3 can sometimes be pulled out by this force. However, when a slit 3s [see FIG. 6 (B)] or notch 3g [see FIG. 6 (A) and FIG. 6 (C)] is formed in the base portion, the amount of force applied to the base end of the internal drainage tube 3 can be reduced. This keeps the internal drainage tube 3 from being pulled out when the external drainage tube 2 is removed.

INDUSTRIAL APPLICABILITY

The biliary tract drainage tube of the present invention can be applied to a device which performs biliary tract drainage using the internal drainage method after performing biliary tract drainage using the external drainage method.

EXPLANATION OF LEGENDS 1. biliary tract drainage tube
2. external drainage tube
2a. main body portion
2b. narrow-diameter portion
3. internal drainage tube
4. detachment-preventing portion
C. gallbladder
Cd. bile duct
D. duodenum
E. endoscope

The invention claimed is:

1. A biliary tract drainage tube used to drain a biliary tract from a patient body, comprising:
   an external drainage tube that is inserted from one of a nose and mouth of the patient body to be placed in a digestive tract, having a first length longitudinally determined between a distal end and a base end, the based end being opposite to the distal end, wherein the first length is large enough to allow the base end to be placed outside the patient body by passing through the one of the nose and mouth while the distal end remains inside a common bile duct of the patient body, and
   an internal drainage tube that is provided on a tip of the external drainage tube so as to be separable from the external drainage tube, having a second length longitudinally determined between a leading end and a trailing end, the tailing end being opposite to the leading end, wherein the leading end is defined as an end closer to the distal end of the external drainage tube than the trailing end, and the second length is large enough to allow the trailing end to protrude into a duodenum of the patient body when the leading end is arranged inside intrahepatic bile ducts of the patient body, wherein
   the external drainage tube comprises a main body portion and a narrow-diameter portion that is provided closer to the distal end of the external drainage tube than the main body portion and longitudinally extends toward the distal end,
   the narrow-diameter portion is integrally formed with the main body portion so as to have an outer diameter that is narrower than an outer diameter of the main body portion such that a step is formed at a boundary between the main body portion and the narrow-diameter portion,
   the narrow-diameter portion has a third length longitudinally determined between the distal end of the external drainage tube and the step at the boundary, and the outer diameter of the narrow-diameter portion is narrower than an inner diameter of the internal drainage tube over the third length such that the narrow-diameter portion is inserted into the inner diameter tube, and the trailing end of the internal drainage tube contacts to the step at the boundary, allowing the internal drainage tube to be pushed forward with the step while the biliary tract drainage tube is inserted into the patient body, and allowing the internal drainage tube to be detached from the narrow-diameter portion when the biliary tract drainage tube is pulled off the patient body.

2. The biliary tract drainage tube according to claim 1, further comprising
   a detachment-preventing portion for preventing the internal drainage tube from the narrow-diameter portion.

3. The biliary tract drainage tube according to claim 2, wherein
   the detachment-preventing portion is placed over the boundary to connect the internal drainage tube and the external drainage tube, and
   is made of one of a fat, protein and water-soluble material, or a combination of at least two of the fat, protein and water-soluble material such that the detachment-preventing portion dissolves in the patient body.

4. The biliary tract drainage tube according to claim 3, wherein
the detachment-preventing portion is threads, tape, and/or an adhesive connecting the internal drainage tube and the external drainage tube.

5. The biliary tract drainage tube according to claim 1, wherein
the third length of the narrow-diameter portion of the external drainage tube
is greater than the second length of the internal drainage tube such that the distal end of the external drainage tube penetrates through the internal drainage tube when the narrow diameter portion is inserted into the internal drainage tube, defining a projecting portion of the narrow-diameter portion that projects from the leading end of the internal drainage tube toward the distal end, and
the projecting portion is curled to be in a ring-shape such that an outer diameter (DA) of the ring-shape is grater than the inner diameter of the internal drainage tube, allowing the internal drainage tube to be held between the ring-shape of the projecting portion and the step at the boundary.

6. The biliary tract drainage tube according to claim 5, wherein
the external drainage tube is configured to have an inner channel through which a guide wire, which is made of metal, penetrates, and
the narrow-diameter portion is made of a material having less rigidity than the guide wire such that the ring-shape of the projecting portion turns into a linear shape when the guide wire goes through the inner channel of the external drainage tube, which includes the narrow-diameter portion.

7. The biliary tract drainage tube according to claim 5, wherein
the projecting portion, which is curled in the ring-shape, is made of a shape memory material of which an original shape at body temperature is in a linear shape so that the ring-shape of the projecting portion becomes straight after being placed in the common bile duct of the patient body.

8. The biliary tract drainage tube according to claim 1, wherein
a connecting portion is provided for connecting the internal drainage tube and the external drainage tube,
the connecting portion is configured so that the connection between the internal drainage tube and the external drainage tube can be severed by ultrasonic stimulation.

9. The biliary tract drainage tube according to claim 8, wherein
the internal drainage tube and the external drainage tube are formed from a single continuous tube.

10. The biliary tract drainage tube according to claim 1, wherein
the internal drainage tube has a slit and/or notch formed in one end thereof, the slit and/or notch extending in an axial direction from the one end.

11. The biliary tract drainage tube according to claim 1, wherein
the outer diameter of the main body portion is the same as an outer diameter of the internal drainage tube such that an outer circumference of the main body portion is flush with an outer circumference of the internal drainage tube at the boundary.

12. The biliary tract drainage tube according to claim 11, wherein
the second length of the internal drainage tube is approximately ranged from 70 mm to 150 mm.

13. The biliary tract drainage tube according to claim 11, wherein
the outer diameter of the main body portion is approximately ranged from 2.7 mm to 3.3 mm.

14. The biliary tract drainage tube according to claim 13, wherein
the inner diameter of the internal drainage tube is approximately ranged from 1.8 mm to 2.5 mm.

15. The biliary tract drainage tube according to claim 14, wherein
the outer diameter of the narrow-diameter portion is approximately ranged from 1.2 mm to 1.5 mm.

16. The biliary tract drainage tube according to claim 11, wherein
in a cross sectional view, the narrow-diameter portion and the internal drainage tube have a circular shape, and
when the narrow-diameter portion is inserted into the internal drainage tube, the narrow-diameter portion and the internal drainage tube are arranged coaxial in the cross sectional view.

17. The biliary tract drainage tube according to claim 1, wherein
a length of the main body portion, which is determined between the step to the base end, is approximately ranged from 2,300 mm to 2,350 mm.

18. A biliary tract drainage tube used to drain a biliary tract from a patient body, comprising:
an external drainage tube that is inserted from one of a nose and mouth of the patient body to be placed in a digestive tract, having a first length longitudinally determined between a distal end and a base end, the based end being opposite to the distal end, wherein the first length is large enough to allow the base end to be placed outside the patient body by passing through the one of the nose and mouth while the distal end remains inside a common bile duct of the patient body, and
an internal drainage tube that is provided at the distal end of the external drainage tube, having a second length longitudinally determined between a leading end and a trailing end, the tailing end being opposite to the leading end, wherein the leading end is defined as an end closer to the distal end of the external drainage tube than the trailing end, and the second length is large enough to allow the trailing end to protrude into a duodenum of the patient body when the leading end is arranged inside intrahepatic bile ducts of the patient body, and
a detachment-preventing part that is a tape in a sheet shape connecting the internal drainage tube to the external drainage tube, wherein
the outer diameter of the external drainage tube is the same as an outer diameter of the internal drainage tube such that an outer circumference of the external drainage tube is flush with an outer circumference of the internal drainage tube at a boundary between the distal end of the external drainage tube and the leading end of the internal drainage tube,
the detachment-preventing part wraps the boundary by entirely surrounding both of the circumferences of the internal and external drainage tubes in order to prevent the internal drainage tube from detaching from the distal end of the external drainage tube, and the detachment-preventing part is made of one of a fat, protein and water-soluble material, or a combination of at least two of the fat, protein and water-soluble material such that the detachment-preventing portion dissolves in the patient body.

\* \* \* \* \*